(12) United States Patent
Malle et al.

(10) Patent No.: US 6,923,953 B2
(45) Date of Patent: Aug. 2, 2005

(54) HAIR TREATMENT METHOD

(75) Inventors: Gérard Malle, Villiers sur Morin (FR); Frédéric Leroy, Saint-Cloud (FR); Yolanda Duvault, Aulnay-sous-Bois (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/055,366

(22) Filed: Jan. 25, 2002

(65) Prior Publication Data

US 2002/0108188 A1 Aug. 15, 2002

Related U.S. Application Data

(62) Division of application No. 09/380,459, filed as application No. PCT/FR98/00420 on Mar. 4, 1998, now Pat. No. 6,361,767.

(30) Foreign Application Priority Data

Mar. 4, 1997 (FR) .............................. 97 02537

(51) Int. Cl.$^7$ ............................ A61K 7/00; A61K 7/06; A61K 7/46
(52) U.S. Cl. ..................... 424/70.1; 424/70.6; 424/401; 8/405; 8/406
(58) Field of Search ............................... 424/70.1, 70.9, 424/401, 405, 431, 132; 132/202, 208

(56) References Cited

U.S. PATENT DOCUMENTS

| | | | |
|---|---|---|---|
| 3,396,736 A | | 8/1968 | Shansky |
| 3,892,845 A | * | 7/1975 | Cunningham et al. ......... 424/62 |
| 3,966,397 A | * | 6/1976 | Leon et al. ...................... 8/10 |
| 4,041,150 A | * | 8/1977 | Karjala ......................... 424/71 |
| 6,361,767 B1 | * | 3/2002 | Malle et al. ................ 424/70.1 |

FOREIGN PATENT DOCUMENTS

| | | | |
|---|---|---|---|
| EP | 0 331 750 | | 9/1988 |
| EP | 0 331 750 | * | 9/1989 |
| WO | WO 96/03966 | * | 2/1996 |

* cited by examiner

Primary Examiner—Thurman K. Page
Assistant Examiner—S. Tran
(74) Attorney, Agent, or Firm—Nixon & Vanderhye, P.C.

(57) ABSTRACT

The invention concerns a method for treating hair keratin fibers to provide them with new appropriate properties, comprising the following steps: reducing the sulphur bonds of hair keratin to generate only at the surface of the fibers at a depth less than 10 μm. reactive sites and in fixing covalently on said reactive sites at least one active compound for providing the hair keratin fibers with new appropriate properties, said active compound containing at least a reactive function capable of reacting with said reactive sites formed at the keratin fiber surface. This method is applicable to the treatment of fibrous or non-fibrous keratin substances of human or animal origin.

29 Claims, No Drawings

HAIR TREATMENT METHOD

The present application is a divisional of application Ser. No. 09/380,459 filed Nov. 22, 1999 which is U.S. Pat. No. 6,361,767 which in turn is a 371 national phase application of PCT/FR98/99429 filed Mar. 4,1998.

The present invention relates to a novel method for treating hair to endow it with novel appropriate properties.

As is well known in the art, the cosmetic qualities of hair can be improved by applying a variety of compositions based on one or more active compounds to endow it with a variety of properties such as, for example, shine, easy disentangling, volume, hold, suppleness, vitality or softness.

To be properly effective, the active compounds of such compositions should, of course, have a certain affinity for the keratinous fibres of the hair, and should also have good persistence.

In other words, such active compounds should as far as possible remain fixed to the hair in a quantity sufficient to endow it with the desired properties.

However, since such active principles are not irreversibly fixed but are only fixed by adsorption, they are gradually eliminated by desorption during successive washes using shampoo.

To improve the persistence, studies have primarily been based on treatments which tend to cause a large proportion of the active principles to penetrate into the fibres, either by selecting such active principles which have a particular affinity for the fibres, or by modifying the fibres to increase their porosity and encourage penetration.

Thus coloration of hair keratin fibres is known to be improved by carrying out coloration simultaneously with permanent-waving. Reduction of the disulphide bonds of the keratin at depth permits the colorant to penetrate deeper and thus produces a certain durability of coloration.

This type of treatment, however, is not without serious disadvantages as it causes substantial degradation not only of the surface condition of the keratinous fibres, but also of their intrinsic mechanical properties.

As a result of a great deal of research in this field with a regard to remedying the disadvantages encountered until now, it has surprisingly and unexpectedly been shown that excellent results could be obtained when fixing active compounds to keratinous hair fibres without them suffering detrimental degradation. This has been achieved by limiting reactive site formation to only the surface of the keratinous hair fibres using a reducing agent employed under conditions and in proportions such that reactive sites are only generated at the periphery of the surface of the keratinous fibres.

It has actually been shown that the creation of reactive sites only on the surface is sufficient, and that they are remarkably reactive, to result in good fixing of a variety of active compounds by means of covalent bonds, without the original mechanical properties of the hair being substantially modified.

Thus the subject of the present invention is a novel method for treating keratinous hair fibres with a view to endowing them with novel appropriate properties, the method comprising steps consisting in reducing the disulphide bonds of the keratin with a view to generating reactive sites only on the surface to a depth of less than 10 $\mu$m and to covalently fix to said reactive sites at least one active compound capable of endowing the keratinous hair fibres with novel appropriate properties, said active compound comprising at least one reactive function capable of reacting with said sites formed at the surface of the keratinous fibres.

In accordance with the invention, the treatment method can be carried out either in two separate steps, namely reducing the disulphide bonds of the keratin in a first step, and fixing the active compound by covalent bonds in a second step, or in a single step consisting in simultaneously reducing the disulphide bonds of the keratin and fixing the active compound.

In a further aspect, the treatment method of the invention envisages first applying the active compound to the keratinous hair fibres and then reducing the disulphide bonds of the keratin.

The essential characteristic of the method of the invention is to form reactive sites only on the surface of the keratinous hair fibres using a reducing composition.

A variety of conventional reducing agents can be used to this end, but their nature and concentration and method of application must be such that reactive sites are only generated on the surface of the keratinous substrate.

In other words, the reducing composition must not react beyond a depth of 10 $\mu$m, preferably not beyond an average depth of 4 to 5 $\mu$m, approximately corresponding to its cuticle.

These are, of course, average values which can vary depending on the type of treatment and which can thus be substantially lower or substantially higher than those indicated.

The reactive sites generated at the surface of the keratinous fibres are nucleophilic in nature and are essentially thiol functions.

In accordance with the invention, the reduction can be such that it generates between 0.1% and 5% by weight of cysteine with respect to the total amino acids of the keratinous fibres, preferably between 0.1% and 2% by weight.

Non limiting examples of hair keratin reducing agents which can be cited are:

thiols such as thioglycolic acid, thiolactic acid, 3-mercaptopropionic acid, thiomalic acid, 2,3-dimercaptosuccinic acid, cysteine, N-glycyl-L-cysteine, L-cysteinylglycine and their esters and salts, thioglycerol, cysteamine and its $C_1$–$C_4$ acylated derivatives, N-mesylcysteamine, N-acetylcysteine, N-mercaptoalkylamides of sugars such as N-(2-mercaptoethyl)gluconamide, pantetheine, the N-(mercaptoalkyl)-ω-hydroxyalkylamides described in patent application EP-A-0 354 835, the N-mono or N,N-dialkyl-4-mercapto butyramides described in patent application EP-A-0 368 763, the aminomercaptoalkylamides described in patent application EP-A-0 432 000, the derivatives of N-mercaptoalkyl) succinamic acid and N-(mercaptoalkyl)succinimides described in patent application EP-A-0 465 342, the alkylamino mercaptoalkylamides described in patent application EP-A-0 514 282, the azeotropic mixture of 2-hydroxypropyl thioglycolate and (2-hydroxy-1-methyl)ethyl thioglycolate described in patent application FR-A-2 679 448, the mercaptoalkylaminoamides described in patent application FR-A-2 692 481, and the N-mercaptoalkylalkanediamides described in patent application EP-A-0 653 202;

hydrides such as sodium or potassium borohydride;

alkali or alkaline-earth metal sulphites or bisulphites;

phosphorus derivatives such as phosphines or phosphites;

hyperbranched polymers and dendrimers carrying terminal thiol functions, such as those described in patent application FR 97 04085 and having formula (I):

$$\text{HS}-\text{A}-\overset{\overset{Y}{\|}}{\text{C}}-\text{X}- \qquad (I)$$

where:
- Y represents an oxygen atom or an NH group;
- A represents a linear, branched or cyclic, saturated or unsaturated $C_1$–$C_{12}$ alkane di-yl group;
- this alkane di-yl group can optionally be interrupted by one or more heteroatoms, such as O or N;
- this alkane di-yl group can optionally be substituted by:
  - an amino function: —$NH_2$, optionally in the form of a salt of a mineral or organic acid;
  - an acylamino function: —NH—COR, where R represents a linear, branched or cyclic, saturated or unsaturated $C_1$–$C_{10}$ alkyl group;
  - a carboxylic acid function;
  - a $C_1$–$C_{10}$ ester function;
- X represents a nucleophilic group.

In a particular preferred embodiment of the method of the invention, the reducing agent is a phosphine or a salt of a phosphine and a mineral or organic acid.

Among the phosphines which have provided particularly advantageous results as regards the formation of reactive sites on the surface of keratinous hair fibres, mention may be made of those with formula:

$$P\begin{array}{c}R_1\\-R_2\\R_3\end{array} \qquad (II)$$

where:
$R_1$, $R_2$ and $R_3$, which are identical, represent:
(a) —$(CH_2)_n$—$CH_3$ (b)
$$-(CH_2)_m-\underset{\underset{R}{|}}{\overset{\overset{R}{|}}{C}}-O-R$$

(c) —$(CH_2)_n$—COOR
(d) —$(CH_2)_n$—CONRR' and
(e) —$(CH_2)_n$—NRR'
n=1 to 3
m=0 or 1 to 3
R and R', which may be identical or different, represent a hydrogen atom or a linear or branched $C_1$–$C_4$ alkyl radical, and salts of said compounds with formula (I).

Salts of phosphines with formula (I) which can be cited include hydrochlorides, hydrobromides, sulphates, citrates, oxalates and acetates.

Phosphines with general formula (I) which are particularly preferred and which can be cited include tris(2-carboxyethyl)phosphine and tris(hydroxymethyl)-phosphine which have the particular advantage not only of being odourless and water-soluble but also of being stable towards oxygen.

Phosphines with general formula (I) are known and have been described in particular in patents U.S. Pat. No. 3,754,035 and U.S. Pat. No. 3,489,811, as well as in EP-A-0 339 212 and in the publication by J. A. Burns et al., J.O.C. 56, 2648–2650 (1991).

The reducing agent is preferably used in aqueous solution under conditions such that its penetration is low to limit the reduction of disulchide bonds to the surface only.

When using a thiol such as thioglycolic acid, for example, its concentration is generally in the range 0.05 to 0.5 M, the pH of the aqueous solution is preferably in the range 6.5 to 9, and the contact time is generally in the range 1 to 10 minutes and preferably in the range 2 to 5 minutes, the pH being adjusted using an agent selected, for example, from: aqueous ammonia, monoethanolamine, diethanolamine, triethanolamine, 1,3-propanediamine, an alkaline or ammonium carbonate or bicarbonate, an organic carbonate such as guanidine carbonate, or an alkaline hydroxide, or advantageously using a polyquaternary ammonium hydroxide such as:

(a) homopolymers comprising units with the following formula (III) as the principal constituent of the chain:

$$\left[-(CH_2)_t-CH\overset{(CH_2)_k}{\underset{H_2C\overset{\oplus}{\underset{R_4}{N}}CH_2}{\diagup}}\overset{\diagdown}{CHR_6}-CH_2-\right] \overset{\ominus}{OH} \qquad (III)$$

where:
- k and t are equal to 0 or 1, the sum k+t being equal to 1;
- $R_4$ and $R_5$ each independently represent an alkyl radical containing 1 to 22 carbon atoms, a hydroxyalkyl radical where the alkyl group preferably contains 1 to 5 carbon atoms, or an amidoalkyl radical where the alkyl group preferably contains 1 to 5 carbon atoms;
- or $R_4$ and $R_5$, together with the nitrogen atom to which they are attached, can represent heterocyclic radicals such as piperdyl or morpholinyl radicals;
- $R_6$ represents a hydrogen atom or a methyl radical;

(b) quaternary diammonium polymers containing repeat units with formula (IV):

$$\left[-\underset{\underset{R_8}{|}}{\overset{\overset{R_7\ \overset{\ominus}{OH}}{|\oplus}}{N}}-A-\underset{\underset{R_{10}}{|}}{\overset{\overset{R_9\ \overset{\ominus}{OH}}{|\oplus}}{N}}-B-\right] \qquad (IV)$$

where:
- $R_7$, $R_8$, $R_9$ and $R_{10}$, which may be identical or different, represent aliphatic, alicyclic or arylaliphatic radicals containing 1 to 20 carbon atoms or $C_1$–$C_5$ lower hydroxyaliphatic radicals, or $R_7$, $R_8$, $R_9$ and $R_{10}$, taken together or separately, form heterocycles with the nitrogen atoms to which they are attached, optionally containing a second heteroatom other than nitrogen, or $R_7$, $R_8$, $R_9$ and $R_{10}$, represent a linear or branched $C_1$–$C_6$ alkyl radical substituted by a nitrile, ester, acyl, amide or —$COOR_{11}$—Q or —CO—NH—$R_{11}$—Q function where $R_{11}$ is an alkylene and Q is a quaternary ammonium group;
- A and B represent linear or branched, saturated or unsaturated polymethylene groups containing 2 to 20 carbon atoms which may contain, bonded to or interposed in the main chain, one or more aromatic ring(s), one or more oxygen or sulphur atom(s), or sulphoxide, hydroxyl, quaternary ammonium, ureido, amide or ester groups;

A, $R_7$ and $R_8$ can further form a piperazine ring with the two nitrogen atoms to which they are attached; further, if A represents a linear or branched, saturated or unsaturated alkylene or hydroxyalkylene radical, B can also denote a —$(CH_2)_n$—CO—D—OC—$(CH_2)_n$— group where D represents:

(i) a glycol residue with formula —O—Z—O— where Z represents a linear or branched hydrocarbon radical, or a —$(CH_2$—$CH_2$—$O)_x$—$CH_2$—$CH_2$— or —$[CH_2$—CH—$(CH_3)$—$O]_y$—$CH_2$—CH—$(CH_3)$—where x and y represent an integer from 1 to 4 corresponding to a defined and unique degree of polymerization, or any number from 1 to 4 corresponding to a mean degree of polymerization;

(ii) a bis-secondary diamine residue such as a piperazine derivative;

(iii) a bis-primary diamine residue with formula —NH—Y—NH— where Y represents a linear or branched hydrocarbon radical or the divalent radical —$CH_2$—$CH_2$—S—S—$CH_2$—$CH_2$—;

(iv) a ureylene group with formula —NH—CO—NH—;

(v) polyquaternary ammonium polymers constituted by units with formula (V):

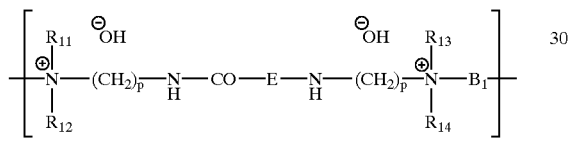

where:

$R_{11}$, $R_{12}$, $R_{13}$ and $R_{14}$, which may be identical or different, represent a hydrogen atom, a methyl, ethyl, propyl, β-hydroxyethyl, β-hydroxypropyl, β-hydroxypropyl or —$CH_2$—$CH_2$—$(O$—$CH_2$—$CH_2)_q$—OH radical, q being an integer from 0 to 6 and $R_{11}$, $R_{12}$, $R_{13}$ and $R_{14}$ not simultaneously being a hydrogen atom;

$B_1$ represents a linear or branched, saturated or unsaturated polymethylene group containing 2 to 20 carbon atoms and containing, bonded to or interposed in the main chain, one or more aromatic ring(s) or one or more oxygen or sulphur atom(s), or sulphoxide, sulphone, disulphide, amino, alkylamino, hydroxyl, quaternary ammonium, ureido, amide or ester groups; $B_1$ preferably represents a radical with formula

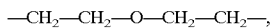

p represents an integer from about 1 to 6;

E can be zero or represent a —$(CH_2)_r$—CO— group where r represents a number equal to 4 or 7.

Of these polymers with formulae (II), (III) and (IV), those which are preferably used are selected from:

the compound with formula (III) where $R_7$, $R_8$, $R_9$ and $R_{10}$ represent the methyl radical; A represents the radical —$(CH_2)_3$— and B represents the radical —$(CH_2)_6$—;

the compound with formula (III) where $R_7$ and $R_8$ represent the ethyl radical, $R_9$ and $R_{10}$ represent the methyl radical and A and B represent —$(CH_2)_3$—;

the compound with formula (III) where $R_7$, $R_8$, $R_9$ and $R_{10}$ represent the methyl radical and A and B represent —$(CH_2)_3$—;

the compound with formula (III) where $R_7$, $R_8$, $R_9$ and $R_{10}$ represent the methyl radical and A and B represent —$(CH_2)_6$—;

the compound with formula (III) where $R_7$, $R_8$, $R_9$ and $R_{10}$ represent the methyl radical; A represents the radical —$(CH_2)_3$— and B represents the radical —$(CH_2)_9$—;

the compound with formula (III) where $R_7$, $R_8$, $R_9$ and $R_{10}$ represent the methyl radical; A represents the radical —$(CH_2)_3$— and B represents the radical —$(CH_2)_2$—O—$(CH_2)_2$—;

the compound with formula (III) where $R_7$, $R_8$, $R_9$ and $R_{10}$ represent the methyl radical; A represents the radical —$(CH_2)_3$— and B represents the radical —$(CH_2)_2$—O—$(CH_2)_2$—O—$(CH_2)_2$—;

the compound with formula (III) where $R_7$, $R_8$, $R_9$ and $R_{10}$ represent the methyl radical; A represents the radical —$(CH_2)_2$—O—$(CH_2)_2$—and B represents the radical —$(CH_2)_2$—O—$(CH_2)_2$—O—$(CH_2)_2$—;

the compound with formula (IV) where $R_{11}$, $R_{12}$, $R_{13}$ and $R_{14}$ represent the methyl radical; $B_1$ represents the radical —$CH_2$—$CH_2$—O—$CH_2$—$CH_2$— and E represents the radical —$(CH_2)_4$—CO—;

the compound with formula (IV) where $R_{11}$, $R_{12}$, $R_{13}$ and $R_{14}$ represent the methyl radical; $B_1$ represents the radical —$CH_2$—$CH_2$—O—$CH_2$—$CH_2$— and E represents the radical —$(CH_2)_7$—CO—;

the compound with formula (IV) where $R_{11}$, $R_{12}$, $R_{13}$ and $R_{14}$ represent the methyl radical; $B_1$ represents the radical —$CH_2$—$CH_2$—O—$CH_2$—$CH_2$— and E has the value zero;

the compound with formula (II) where t=1 and k=0; $R_4$ and $R_5$ represent the methyl radical and $R_6$ represents a hydrogen atom.

The polyquaternary ammonium hydroxides with formulae (II), (III) and (IV) are prepared from the corresponding polyquaternary ammonium halides (the nalide being Cl⁻ or Br⁻) using methods which are known per se, namely:

either exchange with a basic resin such as IRA 400 resin, DOWEX 1×10 resin, etc., in an aqueous medium;

or by precipitation of the halides in the form of silver bromide or chloride using silver oxide $Ag_2O$ in an aqueous medium.

When a hydride such as, for example, potassium borohydride is used, its concentration is generally in the range 0.01 to 0.5 M, the contact time is in the range 1 to 30 minutes, preferably in the range 2 to 15 minutes, and the pH of the aqueous solution is preferably in the range 7.5 to 9.5, the acidifying agent allowing the pH to be adjusted advantageously being boric acid.

When using a phosphorus derivative such as a phosphine, its concentration is generally in the range $10^{-3}$ M to 1 M, preferably in the range $10^{-2}$ M to 0.5 M, the contact time is generally in the range 30 seconds to 1 hour, preferably in the range 1 to 30 minutes, and the pH of the aqueous solution is preferably in the range 3 to 9, more particularly in the range 4 to 7.

When using a hyperbranched polymer or a dendrimer carrying thiol functions, its concentration is generally such that the thiol titre of the solution is generally in the range 100 to 5000 meq/l, preferably in the range 500 to 2000 meq/l, the contact time is generally in the range 30 seconds to 1 hour, preferably in the range 1 to 30 minutes, and the pH of the aqueous solution is preferably in the range 5 to 11, more particularly in the range 7.5 to 10.5.

The disulphide bond reduction step is generally carried out at room temperature, but it can also be carried out at a temperature of less than 60° C.

Clearly, these different parameters concerning the concentration, pH, temperature and contact time are interdependent and clearly, due consideration in this respect should be given. Thus, for example, an increase in the concentration or a rise in temperature will result in a substantial reduction in the contact time.

When the treatment method of the invention is carried out in two steps, after reducing the disulphide bonds of the keratin in the keratinous fibres, they can be rinsed with water before fixing the active compound.

The active compounds which can be covalently fixed on the nucleophilic functions generated can be of a highly varied nature and their choice depends on the desired properties. These active compounds can be used as they are if they possess functions which are capable of forming covalent bonds with the nucleophilic functions of the keratinous hair fibres.

When the active compounds which are to be fixed do not possess such functions, these are then first introduced into the active compound using known methods.

The term "reactive function" means a known reactive group which permits the formation of a covalent bond (by reaction with nucleophilic functions, in this instance sulphydryl functions –SH) and which thus comprise one or more nucleofuge(s) X or one or more activated carbon(s) or bond(s). The following groups are the usual nucleofuges:

Cl, Br, F, —OSO$_3$M, —OSO$_2$ alkyl, —OSO$_2$ aryl, —OSO$_2$N(alkyl)$_2$, —OR$_1$, SR$_2$, —SOR$_2$, —SO$_2$R$_2$, —S$^+$R$_2$R$_3$, —SCN, —SCOOR$_2$, —NR$_2$R$_3$, N$^+$R$_2$R$_3$R$_4$,

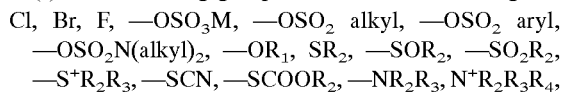

where M represents a hydrogen atom, an alkali or an alkaline-earth metal or an ammonium residue;

R$_1$ represents a hydrogen atom, a C$_1$–C$_4$ alkyl radical, a substituted or unsubstituted phenyl radical, the radical PO$_3$H$_2$ and its salts, or the acetyl radical;

R$_2$, R$_3$ and R$_4$, which may be identical or different, represent a hydrogen atom, a C$_1$–C$_4$ alkyl radical or a substituted or unsubstituted phenyl radical.

Among the most well known reactive groups, the following can be cited:

mono- and dihalotriazines;

dihaloquinoxalines, dihalopyrimidines;

vinylsulphones or their β-halo- or β-sulphatoethylsulphone precursors;

acrylates and methacrylates;

acrylamides and methacrylamides;

maleimides and halomaleimides;

epoxides and aziridine derivatives;

oxazolinium, imadozolium or thiazolidinium groups;

carboxylic or sulphonic acid halides;

esters;

carbamates;

anhydrides;

isothiocyanates and isocyanates;

lactones;

azlactones with structure:

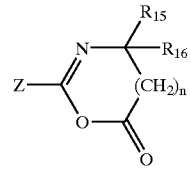

where:

Z represents the residue of an active compound;

R$_{15}$ and R$_{16}$, which may be identical or different, represent a hydrogen atom, a C$_1$–C$_{12}$ alkyl radical, a C$_3$–C$_{12}$ cycloalkyl radical, a C$_5$–C$_{12}$ aryl radical, a C$_6$–C$_{26}$ arenyl radical comprising 0 to 3 heteroatoms selected from S, N and O, or R$_{15}$ and R$_{16}$ together form a carbocycle containing 4 to 12 atoms, and n is an integer in the range 0 to 3, etc.

Among the active compounds which can be covalently fixed on the keratinous hair fibres after reduction of the surface disulphide bonds, those which can be cited are agents which can colour them, protect them from external attacking factors (light, pollution, water), strengthen them, modify their form, give them body, volume, lightness, suppleness, softness or vitality, facilitate combing or disentangling, reduce static electricity or increase their shine, i.e., in general any agent which can protect them and/or improve their appearance and/or feel.

In particular, the following active compounds can be cited by way of example to illustrate the invention:

(a) reactive colorants intended to modify hair colour, such as:

compounds from the REIMAZOL® range sold by DYSTAR;

compounds from the PROCION® range sold by ZENECA;

compounds from the CIBACRONE® and LANASOL® ranges sold by CIBA-GEIGY;

compounds from the LEVAFIX® range sold by BAYER.

The following examples can be cited more particularly:

Reactive Blue 4 (C.I. 61205);

Reactive Black 5 (C.I. 20505);

Reactive Blue 19 (C.I. 61200);

Reactive Orange 16 (C.I. 17757);

Reactive Red 4 (C.I. 18105);

Reactive Yellow 2 (C.I. 18972);

Reactive Yellow 135; and

Reactive Red 2 (C.I. 18200).

(b) reactive sunscreens from the benzylidenecamphor series, para-aminobenzoic acid derivatives and esters thereof, cinnamic acid derivatives and esters thereof, salicyl derivatives, benzophenone derivatives, dibenzoylmethane derivatives, benzotriazole or benzimidazole derivatives, anthranilic acid and its esters, anthranilate or cyanoacrylate derivatives, such as those with the following formulae, for example:

(i)

R' = methyl or tert-octyl (ii)

R'' = H, $C_1$–$C_6$ alkyl, and
Y = NH or O (iii)

$R^1$ = H or OH, and
y $R^2$ = OH or $OCH_3$ (iv)

$R_4$ = H or ——NHCOCH=$CH_2$ (v)

$R_5$ = H or $C_1$–$C_{12}$ alkyl (vi)

(c) reactive shine agents, in particular silicon-containing polymers such as polydimethylsiloxane derivatives having, for example, vinyl, acrylic or epoxy reactive groups, etc. Examples which can be cited are the divinylpolydimethylsiloxanes sold by HÜLS-PETRARCH under reference numbers PS 441, PS 443, PS 445, PS 448 and PS 449.5 or the vinylmethyl polydimethylsiloxane copolymer by the same company under reference number PS 424;

(d) hydrophobic reactive compounds with a $C_8$–$C_{30}$ fatty chain, such as octadecyl methacrylate or acrylate or with a $C_2$ to $C_{18}$ perfluorinated chain, such as the FORALKYLS® AC6 and AC8, MAC6 and MAC8 sold by ELF ATOCHEM, hexafluoropropene oxide, methyl perfluoro-3-buteneoate, etc.

The active compound is generally present in aqueous solution in a concentration in the range $10^{-3}$ to 20%, preferably in the range $10^{-2}$ to 5%, and its pH is generally in the range 2 to 10, preferably in the range 4 to 9.

The contact time necessary for formation of the covalent bonds is generally in the range 1 minute to 1 hour, preferably in the range 1 to 30 minutes at room temperature or at a temperature of less than 60° C.

The composition containing the reducing agent and the composition containing the active compound can also comprise various other additives.

Additives which can be cited in particular include nonionic, anionic, cationic or amphoteric surfactants, volatile or non-volatile, linear or cyclic silicones, polyorganosiloxanes, cationic polymers such as those used in the compositions of patents FR-A-2 472 382 and FR-A-2 495 931 and of patent LU-83703, basic or acidic amino acids, peptides, protein hydrolysates, waxes, $C_3$–$C_6$ alkanediols, $C_1$–$C_5$ lower alcohols, fatty alcohols, fatty acids, alkylene or dialkylene glycol alkyl ethers, glycerol, hydrophilic or lipophilic gelling agents, thickeners, suspension agents, opacifying agents, sequestering agents, colorants, sunscreens, fillers, pigments, odour absorbers, hair loss preventatives, anti-dandruff agents, antioxidants, vitamins, solvents, fragrances and preservatives.

These different additives are generally present in a proportion in the range 0.01% to 20% by weight of the total composition weight.

Some examples of the hair treatment method of the invention will now be given in order to illustrate the invention.

EXAMPLES

Example 1

Method For Fixing a Colorant on Locks of Hair
A. Step for Reducing Hair Locks
Locks of natural hair containing 90% non-pigmented hair were reduced using the following eight methods:
Method 1
A 1 g lock of natural hair was immersed for 5 minutes and at 30° C. in 25 $cm^3$ of an aqueous 0.5 M solution of tris(2-carboxyethyl)phosphine adjusted to a pH of 9 with sodium hydroxide.
Method 2
A 1 g lock of natural hair was immersed for 5 minutes at 30° C. in 5 $cm^3$ of an aqueous 0.5 M solution of tris(2-carboxyethyl)phosphine adjusted to a pH of 8.5 with sodium hydroxide.
Method 3
A 1 g lock of natural hair was immersed for 25 minutes at 30° C. in 5 $cm^3$ of an aqueous 0.1 M solution of tris(2-carboxyethyl)phosphine adjusted to a pH of 8.5 with sodium hydroxide.
Method 4
A 1 g lock of natural hair was immersed for 5 minutes at 30° C. in 25 $cm^3$ of an aqueous 0.1 M solution of sodium borohydride adjusted to a pH of 8.5 with boric acid.
Method 5
A 1 g lock of bleached hair (alkaline solubility=20%) was immersed for 5 minutes at 30° C. in 30 $cm^3$ of an aqueous 0.74 M solution of thioglycolic acid adjusted to a pH of 8 with poly[(dimethyliminio)-1,3-propanediyl (dimethyliminio)-1,6-hexanediyl] dihydroxide.
Method 6
A 1 g lock of natural hair was immersed for 5 minutes at 30° C. in 30 $cm^3$ of an aqueous 1 M solution of L-cysteine containing 7.8 g of poly[(dimethyliminio)-1,3-propanediyl (dimethyliminio)-1,6-hexanediyl] dihydroxide, adjusted to a pH of 9 with aqueous ammonia.

Method 7

A 0.1 g lock of natural hair was immersed in 1 ml of an aqueous solution containing a dendrimer carrying thiol functions, the preparation of which is given below (thiol titre: 1340 meq/l), at a spontaneous pH, for 30 minutes at 30° C.

Preparation of the Dendrimer

540 µl of γ-thiobutyrolactone (i.e., 1 equivalent, calculated with respect to the entirety of the primary amine functions) were added to 2 g of an aqueous 55.7 g/100 g solution of dendrimer sold by DENDRITECH under the name PAMAM STARBURST with a generation 1 ethylenediamine core (8 $NH_2$ functions at the surface) diluted in 2 ml of water, in an inert atmosphere at room temperature. The medium, which was initially heterogeneous, rapidly became homogeneous (1 hour). After 48 hours' stirring, only traces of γ-thiobutyrolactone were detected in the medium. It was washed 3 times with 10 ml of diethyl ether, then nitrogen was bubbled through the aqueous phase thus obtained to eliminate all traces of ether.

The aqueous solution thus obtained was analysed by NMR. It was confirmed that all of the initial primary amine functions were in the form of —NH—CO—$(CH_2)_3$—SH.

The active matter content in this aqueous phase was 37.71 g/100 g.

Molar mass of synthesized product: 2247 g.mol$^{-1}$.

Empirical formula: $C_{94}H_{176}N_{20}O_{20}S_8$.

Method 8

A 0.1 g lock of natural hair was immersed in 1 ml of an aqueous solution containing a branched polyethyleneimine polymer carrying thiol functions, the preparation of which is given below (thiol titre: 1220 meq/l) at a spontaneous pH, for 30 minutes at 30° C.

Preparation of Branched Polyethyleneimine Polymer 1 g of polyethyleneimine with an average molecular weight MW=1200, sold by POLYSCIENCES, was diluted in 3 g of water then 482 µl of γ-thiobutyrolactone (i.e., 6.75 molar equivalents, calculated with respect to the average molecular weight of the polymer) was added in an inert atmosphere at room temperature. The medium, which was initially heterogeneous, rapidly became homogeneous (about 30 minutes). After 2 hours with stirring, no more γ-thiobutyrolactone was detected in the medium. The aqueous phase gave a positive reaction after revealing with sodium nitroprusside. It was thus confirmed that some of the initial primary amine functions were in the form of —NH—CO—$(CH_2)_3$—SH.

The active matter content of this aqueous phase was 34.35 g/100 g.

Molar mass of synthesized product: 1889.6 g/mol$^{-1}$.

After this reduction step, using methods 1 to 8, the locks were rinsed with copious quantities of water.

Surface reduction of the disulohide bonds of the hair keratin using methods 1 to 8 above was demonstrated using a fluorescent probe, 4-(aminosulphonyl)-7-fluoro-2,1,3-benzoxadiazole (ABD-F). This molecule reacts selectively with the keratocysteine formed, giving a fluorescent product. The treatment of transverse microsections of hair by a probe solution thus enabled the reduced zones of the hair to be located.

To this end, the hair reduced using methods 1 to 8 was encased in a fast-setting epoxy resin. 10 µm transverse sections were obtained from the different encased samples produced, using a microtome.

A few drops of the following solution were then applied to the sections: 2.16 mg of ABD-F in 100 ml of a pH 8 borate buffer solution containing 576.8 mg of sodium lauryl sulphate, 37.2 mg of EDTA and 945.5 mg of borax.

This was allowed to react for 30 seconds and the solution was removed using absorbent paper. The sections were then rinsed three times with deionized water then dried and enclosed in Canada balsam.

The fluorescence was observed using a "Diaplan" optical microscope provided wish a filter block to allow excitation at a wavelength λ of 340–380 nm and observation in λ>430 regions. It was thus readily determined that reduction had occurred on the surface to a superficial depth, and not at the interior of the hair keratin fibres.

B. Colorant Graft Step

An aqueous $10^{-2}$ M solution of "Reactive Orange 16" (C.I. 17757) colorant was prepared and the pH was adjusted to 9 with sodium hydroxide. The hair lock reduced using Method 1 above was then immersed in this solution for 30 minutes at 30° C. This operation was then repeated with the other locks reduced using Methods 2 to 8.

The hair locks were then rinsed with copious quantities of water and washed several times with an aqueous 10% solution of sodium lauryl ether sulphate then dried.

Intensely orange coloured locks were thus obtained and it was confirmed that prolonged washing and repeated shampooing did not perceptibly modify the intensity of the coloration with respect to that initially observed.

C. Comparative Study

A 1 g lock of natural hair was immersed for 30 minutes at 30° C. in 25 ml of an aqueous $10^{-2}$ M solution of "Reactive Orange 16" (C.I. 17757) colorant, the pH being adjusted to 9 using sodium hydroxide. The lock was then rinsed with copious quantities of water and washed several times with an aqueous 10% solution of sodium lauryl ether sulphate and dried.

This lock, which had not undergone prior reduction, had a very slight coloration which was only just discernible with the naked eye and this was the same but to a lesser extent when the temperature and contact time were increased.

Example 2

Method For Fixing a Fatty Chain to Hair Locks

A 1 g lock of natural hair which had previously been reduced using Method 1 of Example 1 was immersed in 25 cm$^3$ of a 0.5×10$^{-2}$ M solution of octadecyl methacrylate in an ethanol-water (9/1) mixture and the pH was adjusted to 9 using sodium hydroxide. After 30 minutes at 45° C., the lock was rinsed with copious quantities of ethanol then with deionized water and dried.

Studies carried out on the lock showed that it had a particularly marked hydrophobic nature.

Comparative Study

A 1 g lock of natural hair was immersed for 30 minutes at 45° C. in 25 cm$^3$ of a 0.5×10$^{-2}$ M solution of octadecyl methacrylate in an ethanol-water (9/1) mixture and the pH was adjusted to 9 using sodium hydroxide.

After treatment, the lock was rinsed with copious quantities of ethanol then deionized water and dried.

A study of this lock which had not undergone the prior reduction showed, by wettability measurements, that it had a strong hydrophilic nature. This indicated that there had been no notable fixing of the fatty chain.

Example 3

Method For Fixing a Silicon-containing Polymer to Hair Locks

A 1 g lock of natural hair which had already been reduced using Method 1 of Example 1 was immersed in 25 cm$^3$ of a 1% solution of divinylpolydimethylsiloxane, sold by HÜLS-PETRARCH under the trade name "PS 441®", in an ethanol-water (1/1) mixture and the pH was adjusted to 8 using sodium hydroxide. After 30 minutes at 40° C., the lock was rinsed with copious quantities of water then washed several times with a 10% sodium lauryl ether sulphate solution and dried.

Using wettability measurements, it was confirmed that there had been a substantial reduction in the hydrophilic nature of the lock, it had a much more pleasant feel and it was more shiny.

Example 4

Method For Fixing a Sunscreen to Hair Locks

A. Five 1 g locks of natural brown hair which had already been reduced using Method 2 of Example 1 were immersed in 50 cm$^3$ of an ethanolic 0.1 M solution of [3-benzotriazol-2-yl-2-hydroxy-5-(1,1,3,3-tetramethylbutyl)benzyl]acrylamide heated to 70° C. 20 drops of 0.1 M sodium hydroxide were added and the temperature was maintained for 30 minutes.

After treatment, the locks were rinsed 5 times with 150 cm$^3$ of ethanol then 5 times with 250 cm$^3$ of deionized water and dried.

B. Two 1 g locks of natural brown hair which had already been reduced using Method 3 of Example 1 were immersed in 20 cm$^3$ of a 0.1 M ethanolic solution of [3-benzotriazol-2-yl-2-hydroxy-5-(1,1,3,3-tetramethylbutyl)benzyl]acrylamide heated to 70° C. 8 drops of 0.1 M sodium hydroxide were added and the temperature was maintained for 30 minutes.

After treatment, the locks were rinsed 5 times with 150 cm$^3$ of ethanol then 5 times with 250 cm$^3$ of deionized water and dried.

C. Comparative Study

The locks obtained at A and B above and five locks of natural brown hair as a reference were exposed to artificial light in a XENOTEST 150S simulator for 240 hours. During exposure, the hair was sprayed with water for 5 minutes every 15 minutes.

An examination of the locks after this exposure showed that the locks obtained at A and B, by fixing a sunscreen, exhibited far less degradation of their colour compared with the reference locks. The protective effect was clear after 48 hours of exposure and it was very marked after 240 hours of exposure.

Example 5

Protective Effect of Sunscreens Fixed on Tinted Locks of Hair

Five 1 g locks of 90% naturally white hair which had already been reduced using Method 2 of Example 1 were immersed in 50 cm$^3$ of a 0.1 M ethanolic solution of [3-benzotriazol-2-yl-2-hydroxy-5-(1,1,3,3-tetramethylbutyl)benzyl]acrylamide heated to 70° C. 20 drops of 0.1 M sodium hydroxide were added and the temperature was maintained for 30 minutes.

After treatment, the locks were rinsed 5 times with 150 cm$^3$ of ethanol then 5 times with 250 cm$^3$ of deionized water and dried.

The locks were then tinted using a mixture of 20 g of "MAJIREL 6.1" colorant composition and 30 g of cream oxidizing agent containing 20 volumes of aqueous hydrogen peroxide solution. After leaving for 30 minutes, the locks were rinsed with water then washed with shampoo.

The same treatment was also carried out on 5 locks which had previously been treated using Method 3 of Example 1.

After exposure to the Xenotest under the same conditions as described in Example 4, only a very slight degradation in the colour of the locks was noted compared with the reference locks, i.e., tinted using only the above colorant mixture.

Example 6

Method For Removing Yellow From White Hair

A. Hair Reduction Step

After moistening natural or permed grey hair containing 90% white hairs, the following lotion was applied for 5 minutes at room temperature in an amount of 10 g for every 3 g of hair:

| | | |
|---|---|---|
| Tris (2-carboxyethyl) phosphine | | 14.33 g |
| Hydroxyethylcellulose | | 1.00 g |
| Aqueous ammonia containing 20% NH$_3$ | qs | ph 6 |
| Demineralized water | qs | 100.00 g |

The hair was then rinsed with water and squeezed dripdry.

B. Step for Grafting Yellow-removing Composition 10 g of the following yellow-removing composition were applied for 5 minutes then the hair was rinsed, washed using a standard shampoo and dried.

It was found or seen that the yellowing of the white hair had been completely faded out, while retaining a natural sheen.

Yellow-removing Composition:

| | | |
|---|---|---|
| Procion YELLOW MX-8G ® sold by ZENECA | | 0.01 g |
| Procion RED MX-5B ® sold by ZENECA | | 0.01 g |
| Lanasol blue 3 G sold by CIBA-GEIGY | | 0.01 g |
| Hydroxyethylcellulose | | 1.00 g |
| Lactic acid | qs | pH 4 |
| Demineralized water | qs | 100.00 g |

What is claimed is:

1. Method for fixing a sunscreen or shine agent on hair keratin fibres comprising the stops of reducing the disulphide bonds of the hair keratin with an aqueous reducing agent solution consisting of (1) phosphines or a salt thereof and a mineral or organic acid, wherein the pH of the (1) phosphines solution is in the range 2 to 10 or (2) thiols, wherein the pH of the thiols solution is in the range 6.5 to 9 by using a polyquaternary ammonium hydroxide said reducing agent generating reactive sites only on the surface of said keratin fibres to a depth of less than 10 μm and of covalently fixing on said reactive sites at least one sunscreen or shine agent said sunscreen or shine agent containing at least one reactive function being capable of reacting with said reactive sites formed on the surface of the keratin fibres.

2. Method according to claim 1, wherein in a first step, the disulphidebonds of the keratin are reduced and then in a second step, after optional rinsing with water the sunscreen or shine agent is fixed.

3. Method according to claim 1, wherein the reduction of the disulphide bonds of the keratin is carried out simultaneously with fixing of the sunscreen or shine agent.

4. Method according to claim 1, wherein the reduction of the disulphide bonds is carried out to a depth of about 4 to 5 μm.

5. Method according to claim 1, wherein the reduction is carried out to generate 0.1% to 5% by weight of cystine with respect to the total amino acids of the keratinous hair fibres.

6. Method according to claim 5, wherein reduction is carried out in order to generate 0.1% to 2% by weight of cysteine with respect to the total amino acids of the keratinous hair fibres.

7. Method according to claim 1, wherein the phosphines are of the formula:

 (II)

$R_1$, $R_2$ and $R_3$, which are identical represent:

(a) —$(CH_2)_n$—$CH_3$

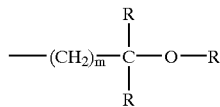 (b)

(c) —$(CH_2)_n$—COOR
(d) —$(CH_2)_n$—CONRR' and
(e) —$(CH_2)_n$—NRR' n=1 to 3
m=0 or 1 to 3

R and R', which may be identical or different, represent a hydrogen atom or a linear or branched $C_1$–$C_4$ alkyl radical and salts of said compounds with formula (II) with a mineral or organic acid.

8. Method according to claim 7, wherein the phosphine salts with formula (II) are selected from the group consisting of hydrochlorides, hydrobromides, sulphates, citrates, oxalates and acetates.

9. Method according to claim 7, wherein the phosphines are selected from the group consisting of tris(2-carboxyethyl)phosphine and tris(hydroxymethyl)phosphine.

10. Method according to claim 7, wherein the phosphines are present in a concentration in the range $10^{-3}$ to 1 M.

11. Method according to claim 7, wherein the pH of the reducing aqueous solution is in the range 3 to 9.

12. Method according to claim 1, wherein the contact time for the aqueous reducing solution with the keratinous fibres is in the range from about 30 seconds to 1 hour, the temperature being in the range from room temperature to a temperature of loss than 60° C.

13. Method according to claim 1, wherein the sunscreen or shine agent is used in an aqueous solution at a concentration in the range from about $10^{-3}$% to 20%, the pH of said solution being in the range from about 2 to 10.

14. Method according to claim 1, wherein the contact time for the aqueous solution of active colorant is in the range from about 1 minute to 1 hour, the temperature being in the range from room temperature to a temperature of less than 60° C.

15. Method according to claim 11, wherein said pH is in the range of 4 to 7.

16. Method according to claim 1 wherein said sunscreen is selected from the group consisting of a benzylidenecamphor, a para-aminobenzoic acid, an ester of a para-aminobenzoic acid, a cinnamic acid, an ester of a cinnamic acid, a sallcilic acid, a dibenzoylmethane, a benzotriazole, a benzimidazole, an anthranilic acid, an ester of an anthranilic acid, an antranilate and a cyanoacrylate; and said shine agent is a silicon-containing polymer.

17. A method of treating keratinous hair fibres comprising (i) reducing disulphide bonds of the hair fibres to generate reactive sites only on the surface of the fibres with an aqueous reducing agent solution, said reducing agent solution being selected from the group consisting of (a) an aqueous solution comprising a hydride present at a concentration of 0.01 to 0.5M, said solution having a pH in the range of 7.5 to 9.5, (b) an aqueous solution comprising a hyperbranched polymer or a dendrimer with a terminal thiol functional groups where the thiol titre is in the range of 100 to 5000 meg/l, said solution have a pH in the range of 5 to 11, and (C) an aqueous solution comprising a thiol present at a concentration of 0.05 to 5M, said solution having a pH in the range of from 6.5 to 9, the pH being adjusted with a polyquaternary ammonium hydroxide;

said reducing further comprising contacting said hair fibres with said aqueous reducing agent for 1 to 30 minutes when said reducing agent is said hydride, or for 30 seconds to 1 hour when said reducing agent is said hyperbranohed polymer or dendrimer, such that said reducing agent generates reactive sites only on the surface of said keratin fibres to a depth of less than 10 μm;

(ii) covalently fixing at least one colorant, sunscreen, shine agent or a hydrophobic reactive compound selected from the group consisting of a $C_8$–$C_{30}$ fatty chain methacrylate, a $C_8$–$C_{30}$ fatty chain acrylate and a $C_2$–$C_{18}$ perfluorinated compound, on said reactive sites formed on the surface of said keratin fibres.

18. The method of claim 17 wherein said hydride is sodium borohydride or potassium borohydride.

19. The method of claim 17 wherein said hyperbranched polymer or dendrimer is a compound of the following formula (I)

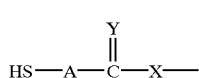 (I)

wherein: Y is an oxygen atom or NH group;

A is a linear, branched or cyclic, saturated or unsaturated $C_1$–$C_{12}$ alkane di-yl group, said alkane di-yl group being optionally interrupted by at least one heteroatom, said alkane di-yl further being optionally substituted by an amino, acylamino, carboxylic acid or ester group; and X is a nucleophilic group.

20. Method according to claim 17, wherein in a first step, the disulphide bonds of the keratin are reduced and then in a second step, after optional rinsing with water the at least one colorant, sunscreen, shine agent or hydrophobic compound is covalently fixed on said reactive sites formed on the surface of said keratin fibres.

21. Method according to claim 17, wherein the reduction of the disulphide bonds of the keratin is carried out simultaneously with fixing of the at least one colorant, sunscreen, shine agent or hydrophobic compound.

22. Method according to claim 17, wherein the reduction of the disulphide bonds is carried out to a depth of about 4 to 5 μm.

23. Method according to claim 17, wherein the reduction is carried out to generate 0.1% to 5% by weight of cysteine with respect to the total amino acids of the keratinous hair fibres.

24. Method according to claim 17, wherein reduction is carried out in order to generate 0.1% to 2% by weight of cysteine with respect to the total amino acids of the keratinous hair fibres.

25. Method according to claim 17 wherein said pH is in the range of 7.5 to 10.5 when said reducing agent is said aqueous solution comprising a hyperbranched polymer or a dendrimer.

26. The method of claim 17 wherein said colorant is selected from the group consisting of Cl 61205, Cl 20505, Cl 61200, Cl 17757, Cl 18105, Cl 18972, Reactive Yellow 135 and Cl 18200.

27. The method according to claim 17 wherein the temperature of the aqueous reducing agent solution is in the range of from room temperature to less than 60° C.

28. The method according to claim 17, wherein the temperature of the aqueous reducing agent solution is room temperature.

29. The method of claim 17 wherein said hydrophobic compound is selected from the group consisting of octadecyl methacrylate, octadecyl acrylate, hexafluoropropene oxide and methyl perfluoro-3-buteneoate.

* * * * *